(12) United States Patent
Xie et al.

(10) Patent No.: US 9,970,894 B2
(45) Date of Patent: May 15, 2018

(54) METHOD AND DEVICE FOR MEASURING CONCENTRATION OF SUBSTANCE IN FLUID

(71) Applicant: SUNVOU MEDICAL ELECTRONICS CO., LTD., Wuxi, Jiangsu (CN)

(72) Inventors: Ray Xie, Jiangsu (CN); Jie Han, Jiangsu (CN); Lijun Shen, Jiangsu (CN); Yiping Han, Jiangsu (CN)

(73) Assignee: Sunvou Medical Electronics Co., Ltd., Woxi, Jiangsu (CN)

( * ) Notice: Subject to any disclaimer, the term of this patent is extended or adjusted under 35 U.S.C. 154(b) by 586 days.

(21) Appl. No.: 14/408,526

(22) PCT Filed: Jun. 20, 2013

(86) PCT No.: PCT/CN2013/000718
§ 371 (c)(1),
(2) Date: Dec. 16, 2014

(87) PCT Pub. No.: WO2013/189175
PCT Pub. Date: Dec. 27, 2013

(65) Prior Publication Data
US 2015/0185177 A1    Jul. 2, 2015

(30) Foreign Application Priority Data

Jun. 21, 2012  (CN) .......................... 2012 1 0207872
Jun. 29, 2012  (CN) .......................... 2012 1 0224156

(51) Int. Cl.
  *G01N 27/26*  (2006.01)
  *G01N 33/00*  (2006.01)
(52) U.S. Cl.
  CPC ......... *G01N 27/26* (2013.01); *G01N 33/0006* (2013.01)

(58) Field of Classification Search
  CPC .............. G01N 27/26; G01N 27/4045; G01N 27/4074; G01N 27/3274; G01N 33/0006;
  (Continued)

(56) References Cited

U.S. PATENT DOCUMENTS

| 4,829,809 A | 5/1989 | Tantram et al. |
| 4,833,909 A | 5/1989 | Matthiessen |

(Continued)

FOREIGN PATENT DOCUMENTS

| CN | 101368921 A | 2/2009 |
| CN | 101368927 A | 2/2009 |

(Continued)

OTHER PUBLICATIONS

PCT International Search Report, PCT/CN2013/000718 dated Oct. 3, 2013.

*Primary Examiner* — Gurpreet Kaur
(74) *Attorney, Agent, or Firm* — TraskBritt, P.C.

(57) ABSTRACT

A method and device for measuring a substance's concentration in a fluid. The method includes first passing a sample to be measured through a chemical sensor at least twice and recording the response value each time; forming a simultaneous equation set using the equation relation between the response value obtained during each measurement and the concentration of the substance, and the mass equation relation satisfied by the concentration change caused by a physical, chemical reaction during each measurement and by the change of the mass, electric quantity, and heat; solving for the concentration of the substance measured and the sensor calibration parameter. The method, used as an absolute measurement method, can be applied to calibrate the sample concentration of a fluid, overcomes the effects on the measurements caused by temperature, humidity, pressure, and some interfering gas, requires no sensor calibra- (Continued)

tion, and substantially enhances the measurements' stability and reliability.

3 Claims, 3 Drawing Sheets

(58) Field of Classification Search
CPC .............. G01N 33/497; G01N 33/007; G01N 33/4925; A61B 5/14542
See application file for complete search history.

(56) References Cited

U.S. PATENT DOCUMENTS

| | | |
|---|---|---|
| 6,055,840 A | 5/2000 | Warburton |
| 6,918,281 B2 | 7/2005 | Sussman et al. |
| 7,071,386 B2 | 7/2006 | Bintrim et al. |
| 7,401,493 B2 | 7/2008 | Forrest |
| 7,581,425 B2 | 9/2009 | Forrest |
| 7,645,362 B2 | 1/2010 | Kato et al. |
| 7,655,186 B2 | 2/2010 | Tobias |
| 7,661,290 B2 | 2/2010 | Gu et al. |
| 7,704,356 B2 | 4/2010 | Kühn et al. |
| 7,975,525 B2 | 7/2011 | Bonne et al. |
| 2004/0082872 A1 | 4/2004 | von Bahr et al. |
| 2005/0241959 A1 | 11/2005 | Ward et al. |
| 2005/0262924 A1 | 12/2005 | Wood |
| 2006/0042351 A1 | 3/2006 | Liu et al. |
| 2006/0266097 A1 | 11/2006 | Eickhoff |
| 2007/0079025 A1 | 4/2007 | Gloekler et al. |
| 2011/0197649 A1* | 8/2011 | Han ................ G01N 33/0006 73/1.06 |

FOREIGN PATENT DOCUMENTS

| | | |
|---|---|---|
| CN | 101393199 A | 3/2009 |
| CN | 102778541 A | 11/2012 |
| CN | 202631479 U | 12/2012 |
| CN | 202631480 U | 12/2012 |
| CN | 202676655 U | 1/2013 |
| CN | 202676656 U | 1/2013 |
| CN | 202676663 U | 1/2013 |
| CN | 202693516 U | 1/2013 |
| WO | 2007079025 A2 | 7/2007 |
| WO | 2013189175 A1 | 6/2013 |

* cited by examiner

METHOD AND DEVICE FOR MEASURING CONCENTRATION OF SUBSTANCE IN FLUID

CROSS-REFERENCE TO RELATED APPLICATIONS

This application is a national phase entry under 35 U.S.C. § 371 of International Patent Application PCT/CN2013/000718, filed Jun. 20, 2013, designating the United States of America and published in English as International Patent Publication WO2013/189175 A1 on Dec. 27, 2013, which claims the benefit under Article 8 of the Patent Cooperation Treaty to China Application Serial Nos. 201210207872.6, filed Jun. 21, 2012, and 201210224156.9, filed Jun. 29, 2012.

TECHNICAL FIELD

The disclosure relates to a method and a device for measuring material concentration in a fluid, which can be used as an absolute measurement method for calibrating the concentration of a gas/liquid sample.

BACKGROUND

A method for measuring the material concentration $C_0$ with a chemical sensor is based on a measurement equation of the response signal $S_0$:

$$S = f(C0; k0, k1 \ldots kp-1) \quad (1)$$

Wherein, the parameters $k_j$ depend on the structural properties of the sensor, the composition of the sample, and the temperature, pressure, and flow state of the sample and environment. The current signal S of the most commonly used electrochemical, semiconductor, and catalyst-based sensor usually meets the following measurement equation:

$$S = kC_0 + k_0 \quad (2)$$

Wherein, parameters $k_0$ and k are zero point and sensitivity parameter of a sensor, respectively.

In the actual application of a sensor, the response signal of the sensor may be affected by factors such as the gas flow rate, pressure, temperature, and humidity, and other gas components, and the sensitivity of the sensor may vary owing to ageing, inactivation, activation, or poisoning, etc. Therefore, a sensor usually has to be calibrated with at least two standard samples with known concentration under conditions close to the actual application conditions, including gas flow rate, pressure, temperature, humidity, and gas components before it can be used, in order to ascertain the applicability of the equation (1) and the parameters $k_j$ of the sensor; in addition, the time of calibration should be close to the time of measurement as far as possible, to avoid the interferences described above.

In actual application, the calibration process involves a series of problems, for example, there are technical and safety risks, since it is difficult to prepare, store, carry or use calibration samples with low concentration, high volatility, high reactivity, and high hazards (toxic, harmful, flammable, and explosive); there are risks related with reliability and effectiveness, since it is usually difficult to simulate the actual situation with the calibration sample and calibration conditions; even though the actual situation can be simulated in the calibration process, it is difficult to carry out calibration at the site of application; even though the calibration can be carried out on site, many user usually neglect calibration. For example, it is difficult to obtain or use calibration samples of organic volatile materials, such as formaldehyde and benzene, etc. It is difficult to carry out calibration on site even in the industrial and environmental safety monitoring field where on-site calibration is applied most widely, especially at coal and oil gathering and transportation sites. Safety accidents incurred by misreport or concealment often occur owing to negligence or improper calibration. Especially, in the civilian field, such as blood glucose test and indoor gas leakage warning, etc., in household application, calibration is seldom carried out, and the resulting accidents are often reported.

At present, efforts made to solve that problem mainly involve providing safe, convenient, and reliable automatic calibrators. For example, in recent years, Honeywell disclosed a number of patents related with sensor calibration and automatic calibration methods (U.S. Pat. No. 7,975,525B2, U.S. Pat. No. 7,661,290B2, US2006/0266097A1, US2005/0262924A1, U.S. Pat. No. 7,401,493B2, U.S. Pat. No. 7,581,425B2, U.S. Pat. No. 7,655,186B2, U.S. Pat. No. 7,071,386B2, U.S. Pat. No. 6,918,281, US2006/0042351A1), and Drager has disclosed several patents related with sensor calibration (U.S. Pat. No. 7,704,356B2, U.S. Pat. No. 7,645,362B2) lately a common characteristic of these patents is that a standard gas is required, while only the method for producing the standard gas varies among these patents. Is there any calibration method that doesn't require a standard gas?

In 1987 and 1989, City Tech and Drager, respectively, disclosed patents (U.S. Pat. No. 4,829,809, U.S. Pat. No. 4,833,909) in which calibration could be carried out without a calibration sample, an electrochemical sensor is placed in an enclosed container filled with a sample, the gas concentration is ascertained through coulomb electrolysis after the tested material is completely electrolyzed, and thereby the sensor is calibrated.

In 2000, Industrial Scientific discloses a patent (U.S. Pat. No. 6,055,840), in which a method for determining the gas concentration by regulating and controlling the resistance in a gas diffusion channel quantitatively was described. However, that method is also inconvenient to use in actual application, because the diffusion coefficient of the tested gas and at least one physical dimension of a gas diffusion channel must be known.

These methods still belong to methods for laboratory research or analysis, and are difficult to use in actual application. At present, the calibration of gas sensors still rely on a calibration method in which materials with standard concentration provided by a standard measurement department are used.

BRIEF SUMMARY

In view of the drawbacks in the prior art, the disclosure puts forward a method and a device for measuring the absolute value of material concentration in a fluid, which utilize the intrinsic characteristics of a sensor and physical and chemical laws, and don't have to use standard materials to calibrate the characteristics of the sensor.

The method can be expressed as follows:

Driving a sample to be tested to pass through a chemical sensor at least twice, and logging the response value of the chemical sensor in each time; establishing a simultaneous system of equations from the measurement equation relationship between the response signal of the sensor obtained in each measurement and the concentration of the sample and the mass equation relationship between the concentration change of the sample resulted from physical and chemical reactions in each measurement and the change of mass, electric quantity, and heat, and solving the simultaneous system of equations to ascertain the concentration of the tested sample and the calibration parameters of the sensor.

When an electrochemical sensor is used in the measurement, the method can be expressed as:

Driving a sample to be tested to pass through an electrochemical sensor at least twice, and logging the response value of the electrochemical sensor in each time; establishing a simultaneous system of equations from the measurement equation relationship between the current value of the electrochemical sensor obtained in each measurement and the concentration of the sample and the mass equation relationship between the concentration change of the sample resulted from electrolysis and the consumed electric quantity, and solving the simultaneous system of equations to ascertain the concentration of the tested sample and the calibration parameters of the sensor.

A device that implements the measurement method described above consists of a sample chamber, an electrochemical sensor, a pump, and a valve, when the device is used for analysis of gas concentration, the sample chamber, electrochemical sensor, pump, valve, and a pipeline form a circulating flow path; the sample chamber is a slender pipeline, in which a gas flows in a manner of piston flow in the process of analysis, the volume of the sample chamber is greater than 95% of the total volume of the circulating flow path, and the sample chamber is used to store the fluid sample to be analyzed; the electrochemical sensor is enclosed in the circulating flow path, and is used to measure a response signal and electrolyze the electrochemical active component to be measured; the pump is used to drive the fluid to circulate in the circulating flow path, so that the fluid can pass through the sensor at least twice.

Another device that implements the measurement method described above consists of a piston sample chamber, a three-way valve, an electrochemical sensor, and a buffer chamber, wherein, the piston sample chamber, three-way valve, electrochemical sensor, and buffer chamber are connected in series through a pipeline, and one way of the three-way valve is used to receive a sample to be analyzed; the piston sample chamber is used to store the fluid to be analyzed and drive the fluid to flow to and fro in the pipeline and the sensor at a constant flow rate; the electrochemical sensor is used to measure a response signal and electrolyze the electrochemical active component to be measured; the buffer chamber is used to store the fluid.

In another method disclosed in the disclosure, the zero point of a sensor is obtained by measurement, specifically, the method driving a sample to be tested to pass through an electrochemical sensor at least twice, and logging the response current value of the electrochemical sensor in each time, wherein, one of the two measurements is used to measure the zero point of the sensor; establishing a simultaneous system of equations from the measurement equation relationship between the current value of the electrochemical sensor obtained in each measurement and the concentration of the sample and the mass equation relationship between the concentration change of the sample resulted from electrolysis and the consumed electric quantity, and solving the simultaneous system of equations to ascertain the concentration of the tested sample and the calibration parameters of the sensor.

To implement the method described above, the disclosure discloses the following four types of devices.

A device that implements the measurement method described above consists of a sample chamber, a small gas chamber, an electrochemical sensor, a pump, and a valve, wherein, the sample chamber, electrochemical sensor, pump and valve are connected through a pipeline to form a circulating gas path, in the circulating gas path, the electrochemical sensor is connected with the pump in series, the small gas chamber is connected in parallel via the valve at the other end of the pump and the other end of the electrochemical sensor, and the volume of the small gas chamber is smaller than $1/10$ of the volume of the sample chamber; the sample chamber is a slender pipeline, the volume of the sample chamber is greater than 95% of the total volume of the circulating gas path, a gas flows in the sample chamber in a manner of piston flow in the process of analysis, and the sample chamber is used to store the fluid sample to be analyzed; the electrochemical sensor is enclosed in the circulating flow path, and is used to measure a response signal and electrolyze the electrochemical active component to be measured; the pump is used to drive the fluid to circulate in the circulating flow path, so that the fluid can pass through the sensor at least twice.

Another device that implements the measurement method described above consists of a sample chamber, a capillarity tube, an electrochemical sensor, a pump, and a valve, wherein, the sample chamber, electrochemical sensor, pump and valve are connected through a pipeline to form a circulating gas path; the sample chamber is a slender pipeline, in which a gas flows in a manner of piston flow in the process of analysis, the volume of the sample chamber is greater than 95% of the total volume of the circulating gas path, and the sample chamber is used to store the fluid sample to be analyzed; the electrochemical sensor is enclosed in the circulating flow path, the gas inlet and gas outlet that communicate with the sensor are provided by the capillarity tube, the ratio of the cross-sectional area to the length of the capillarity tube is smaller than 5% of the ratio of the apparent area of poles of the sensor to the thickness of the gas chamber; the electrochemical sensor is used to measure a response signal and electrolyze the electrochemical active component to be measured; the pump is used to drive the fluid to circulate in the circulating flow path, so that the fluid can pass through the sensor at least twice.

Yet another device that implements the measurement method described above forms a circulating flow path consisting by a sample chamber, a filter, an electrochemical sensor, a pump, and a valve, wherein, the sample chamber, electrochemical sensor, pump and valve are connected through a pipeline to form a circulating gas path, the filter is connected in parallel via the valve in front of the gas inlet of the sensor in the pipeline; the sample chamber is a slender pipeline, a gas flows in the sample chamber in a manner of piston flow in the process of analysis, the volume of the sample chamber is greater than 95% of the total volume of the circulating gas path, and the sample chamber is used to store the fluid sample to be analyzed; the electrochemical sensor is enclosed in the circulating flow path, and is used to measure a response signal and electrolyze the electrochemical active component to be measured; the pump is used to drive the fluid to circulate in the circulating flow path, so that the fluid can pass through the sensor at least twice.

Still another device that implements the measurement method described above consists of a first sample chamber, a second sample chamber, an electrochemical sensor, pumps, and valves, wherein, the first sample chamber, electrochemical sensor, a pump and a valve are connected through a pipeline to form a first circulating gas path; the second sample chamber, a filter, a pump and a valve are connected through a pipeline to form a second circulating gas path, and the two circulating gas paths are connected in parallel with each other; the sample chamber is a slender pipeline, the volume of the sample chamber is greater than 95% of the total volume of the circulating gas path, a gas flows in the sample chamber in a manner of piston flow in the process of analysis, and the sample chamber is used to store the fluid sample to be analyzed; the electrochemical sensor is enclosed in the circulating flow path, and is used to measure a response signal and electrolyze the electrochemical active component to be measured; the pump is used to drive the fluid to circulate in the circulating flow path, so that the fluid can pass through the sensor at least twice.

The method is an absolute concentration measurement method, and it overcomes the effect of temperature, humidity, pressure, and some interfering gas to the measurement, and doesn't require calibration of the sensor, thus, it greatly improves the stability and reliability of the measurement.

With the device described above, the zero point of the sensor can be measured directly on site; thus, it is unnecessary to carry out zero calibration for the sensor with zero gas before the measurement, therefore, the measuring process is simplified, the data processing complexity is decreased, a stage of error propagation is eliminated, and thereby the reliability and repeatability of the measurement result are further improved.

BRIEF DESCRIPTION OF THE DRAWINGS

To make the content of the disclosure understood more clearly, hereunder the disclosure will be further detailed according to some embodiments, with reference to the accompanying drawings, wherein.

Among the figures: 1—first valve, 2—second valve, 3—third valve, 4—fourth valve, 5—first pump, 6—electrochemical sensor, 7—sample chamber, 8—small gas chamber, 9—second pump, 10—third pump, 11—second filter, 12—second sample chamber, 13—piston sample chamber, 14—three-way valve, 15—electric buffer chamber, 16—filter.

DETAILED DESCRIPTION

Embodiment 1

Figure 1:
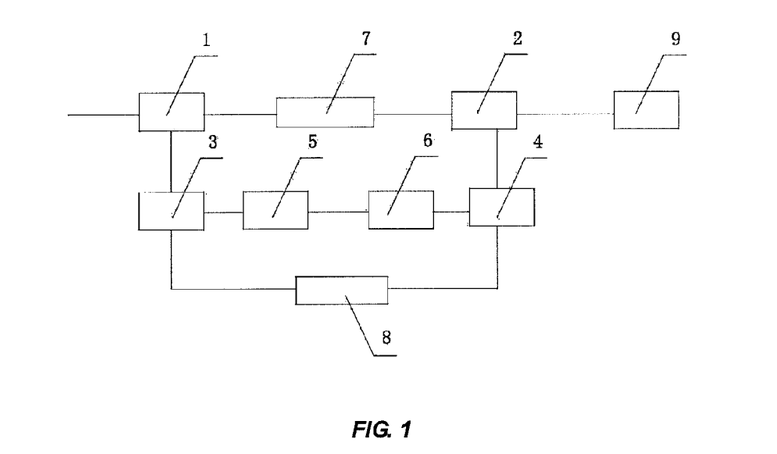
FIG. 1 is a schematic structural diagram of the device in embodiment 1 of the disclosure.

Please see FIG. 1.

The device consists of a sample chamber 7, an electrochemical sensor 6, a first pump 5, a second pump 9, and a first valve 1, a second valve 2, a third valve 3, and a fourth valve 4, wherein, the sample chamber 7, electrochemical sensor 6, first pump 5, and first valve 1, second valve 2, third valve 3, and fourth valve 4 are connected through a pipeline to form a closed circulating flow path; the pipeline is composed of capillary tubes, and the internal volume of the capillary tube is smaller than 5% (equal to 4%) of the total volume of the circulating flow path; the sample chamber 7 is constructed in a way that a gas flows in it in a manner of piston flow in the process of analysis, the sample chamber 7 is a slender pipeline in structure, and the total volume of the sample chamber 7 is greater than 95% (equal to 96%) of the total volume of the circulating flow path; the electrochemical sensor is enclosed in the circulating flow path, and is used to measure a response signal and electrolyze the electrochemical active component to be measured; the pump is used to drive the gas to circulate in the circulating gas path, and the flow rate of the circulating gas can be obtained from the volume of the gas chamber and the cycle period; a small gas chamber 8 connected in parallel with the first pump 5 beside the electrochemical sensor 6, third valve 3, and fourth valve 4 are used to measure the zero point of the sensor on site, and the volume of the smaller gas chamber 8 is smaller than $1/10$ of that of the sample chamber 7.

The actual measurement process is carried out through the following three steps:

(1) Sampling: switch the first valve 1 and second valve 2, and pump a gas with the second pump 9 via the first valve 1, sample chamber 7, second valve 2 and second pump 9 into the sample chamber 7.

(2) Circulation and measurement: switch the first valve 1, second valve 2, third valve 3, and fourth valve 4 and start the first pump 5 at the same time, so that the gas flows through the first pump 5, electrochemical sensor 6, fourth valve 4, second valve 2, sample chamber 7, first valve 1, second valve 2, returns to the electrochemical sensor 6, and circulates in that way, when sample under the action of the circulating pump, and carry out analysis and measurement in two circulations, wherein, the gas is electrolyzed when it passes through the sensor, and the measurement equation met by the response value of the sensor whenever the gas passes through the sensor can be expressed as:

$$i_0 = kC_0 + k_0 \quad (2)$$

$$i_1 = kC_1 + k_0 \quad (3)$$

Wherein, $i_0$ and $i_1$ are response values of the sensor in the two measurements, k is the sensitivity of the sensor, $k_0$ is the background current of the sensor, $C_0$ and $C_1$ are initial concentration of the sample and concentration of the sample measured in the second measurement, respectively; the unknown quantities are k, $k_0$, $C_0$, and $C_1$.

According to Faraday's law, the mass equation of the relationship between the quantity of sample consumed by electrolysis and the resultant change of concentration of the sample in each measurement carried out by the sensor can be expressed as:

$$nFV(C_1 - C_0) = i_0 * t \quad (4)$$

Wherein, n is the number of electronics involved in the reaction, F is Faraday constant, V is the volume of the sample chamber, and t is the cycle period.

(3) Measurement of zero point: after twice measurements are completed, switch the solenoid valves 3 and 4 to change the gas flow direction to 5, 6, 4, 8, 3 and 5, in this case, the sensor carries out exhaustive electrolysis of the active gas component in the small circulating gas path, and the response value of the sensor will approach to the zero response value $k_0$ of the sensor after a period that is long enough.

Thus, the sample concentration $C_0$ and the sensor sensitivity k can be solved from the simultaneous equations (2), (3), (4) and directly measured $k_0$.

It is seen from this embodiment: the method can be used to directly ascertain the concentration of the measured material, without calibrating the sensor before the measurement; in addition, the calibration parameters (e.g., sensitivity and background current) of the sensor can be directly solved with the method. Since the sensor calibration parameters are calculated in an actual measurement process, the method can be regarded as a self-calibration method. In addition, since the method utilizes the difference between two response values of the sensor, the contributions of temperature, pressure, flow, and interfering materials, which are identical in each measurement, is deducted, therefore, compared with the conventional method, which utilizes signals that contain these contributing factors, the method has higher sensitivity, selectivity, and stability.

The implementation of the method has requirements for gas path structure, gas path resistance and sensor sensitivity. Generally speaking, the resistance in the bigger circulating gas path and the resistance in the smaller circulating path must be essentially equal to each other, in order to ensure the gas flow rate in zero measurement is essentially equal to flow rate in the concentration measurement. In addition, two criteria must be met in the selection of sensitivity of the sensor, on the one hand, the sensitivity must be appropriate (not too high or too low), to ensure that the change of concentration gradient resulted from each circulation cycle of the gas in the major circulation and analysis process is distinguishable and the concentration will not be decreased too severely after several circulation cycles; on the other hand, on the premise that the first criterion is met, the sensitivity should be high enough, so that the active gas in the small circulating gas path can be depleted in a short time period.

Four valves are used in this embodiment to control the gas flow direction and on/off. Apparently, the first valve 1 and third valve 3 can be replaced with a two-position three-way valve, and the second valve 2 and fourth valve 4 can also be replaced with a two-position three-way valve, so as to reduce the elements in the gas path.

Embodiment 2

Figure 2:
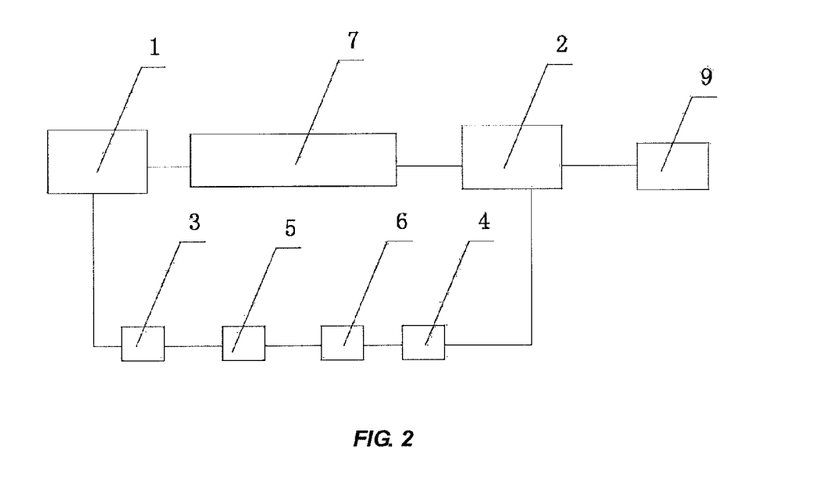
FIG. 2 is a schematic structural diagram of the device in embodiment 2 and 5 of the disclosure.

FIG. 2 shows a second gas path design that implements the measurement method disclosed in the disclosure. The device comprises a sample chamber 7, an electrochemical sensor 6, a first pump 5, a first valve 1, a second valve 2, a third valve 3 and a fourth valve 4, wherein, the sample chamber 7, electrochemical sensor 6, first pump 5, first valve 1 and second valve 2 are connected through a pipeline to form a circulating gas path; the sample chamber 7 is a slender pipeline, in which a gas flows in a manner of piston flow in the process of analysis, the volume of the sample chamber is greater than 95% (equal to 98%) of the total volume of the circulating gas path, and the sample chamber 7 is used to store the fluid sample to be analyzed; the electrochemical sensor is enclosed in the circulating flow path, the gas inlet and gas outlet that communicate with the sensor are provided by capillarity tubes, the ratio of the cross-sectional area to the length of the capillarity tube is smaller than 5% (equal to 2%) of the ratio of the apparent area of poles of the sensor to the thickness of the gas chamber, the electrochemical sensor is used to measure a response value and electrolyze the electrochemical active component to be measured; the pump 5 is used to drive the fluid to circulate in the circulating flow path, so that the fluid can pass through the sensor at least twice.

The actual measurement process is carried out through the following steps:

(1) Sampling: adjust the state of the first valve 1, second valve 2, third valve 3 and fourth valve 4, and start the first pump 5 and second pump 9, so that the gas passes through the first valve 1, sample chamber 7, second valve 2 and second pump 9, and is collected into the sample chamber 7, the gas in the other way passes through the first valve 1, third valve 3, first pump 5, electrochemical sensor 6, fourth valve 4, second valve 2 and second pump 9, and flows out.

(2) Measurement of zero point: close the first valve 1, second valve 2, third valve 3 and fourth valve 4, and stop the first pump 5 and second pump 9, and hold the gas for a while; in that state, the sensor keeps depleting the active gas in the small gas chamber of the sensor by electrolysis; after a time period that is long enough, the response value of the sensor will be the zero response value.

(3) Circulation and measurement: after the zero response value is obtained, start the first pump 5 and adjust the state of the valves, so that the gas circulates in the circulating gas path constituted by the sample chamber 7, first pump 5, electrochemical sensor 6, and sample chamber 7 to carry out a plenty of analysis cyclically.

The implementation of the method has requirements for gas path structure and sensor sensitivity, i.e., the volume of cavity in the sensor must be small enough, the contact area between the gas electrodes of the sensor and the sample must be large enough, the gas inlet and gas outlet that communicate with the sensor must be provided by capillary tubes, and the ratio of the cross-sectional area to the length of the capillary must be smaller than 1% of the ratio of the apparent area of poles of the sensor to the thickness of the gas chamber. Thus, the gas diffusion process can be neglected when there is no forced convection, and the sensor can accomplish electrolysis of 99% of active component in a required time period. The sensitivity of the gas sensor must be appropriate (not too high or too low), in order to ensure that the change of concentration gradient resulted from each gas circulation cycle in the cyclic analysis process is distinguishable and the concentration will not be decreased too severely after several circulation cycles. Of course, the gas inlet and gas outlet that communicate with the sensor may not be implemented by means of capillary tubes; instead, the communication between the sensor and the gas path can be cut off by means of a solenoid valve in the measurement of zero point.

Embodiment 3

Figure 3:
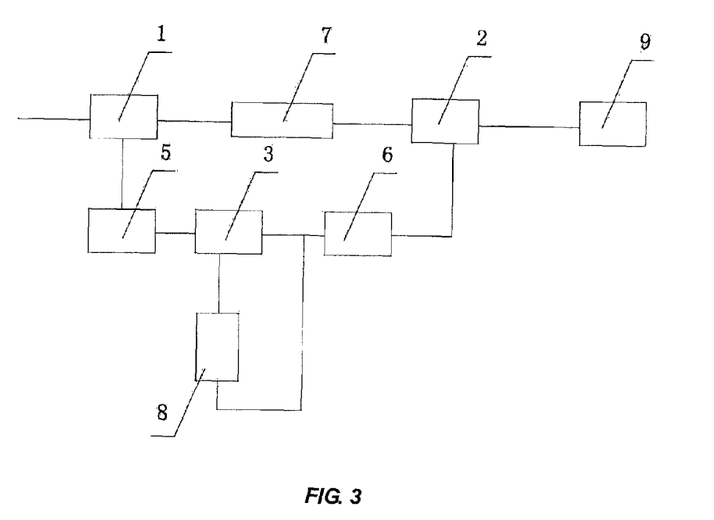
FIG. 3 is a schematic structural diagram of the device in embodiment 3 of the disclosure.

FIG. 3 shows a third gas path design that implements the measurement method disclosed in the disclosure. The device forms a circulating flow path by a sample chamber 7, a filter 16, an electrochemical sensor 6, a first pump 5, a first valve 1, a second valve 2 and a third valve 3, wherein, the sample chamber 7, electrochemical sensor 6, first pump 5, first valve 1, second valve 2 and third valve 3 are connected through a pipeline to form a circulating gas path; the filter is connected in parallel via the third valve 3 in front of the gas inlet of the sensor in the pipeline; the sample chamber 7 is a slender pipeline, a gas flows in the sample chamber 7 in a manner of piston flow in the process of analysis, the volume of the sample chamber 7 is greater than 95% (equal to 99%) of the total volume of the circulating gas path, and the sample chamber 7 is used to store the fluid sample to be analyzed; the electrochemical sensor is enclosed in the circulating flow path; the pump is used to drive the fluid to circulate in the circulating flow path, so that the fluid can pass through the sensor at least twice.

The actual measurement process is carried out through the following steps:

(1) Sampling: switch the first valve 1 and second valve 2, and start the second pump 9, so that the gas passes through the first valve 1, sample chamber 7, second valve 2, and second pump 9, and is collected into the sample chamber 7;

(2) Circulation and measurement: switch the first valve 1 and second valve 2, and start the first pump 5, so that the gas circulates in the circulating gas path constituted by the sample chamber 7, first pump 5, third valve 3, electrochemical sensor 6, and sample chamber 7 to carry out a plenty of analysis cyclically.

(3) Measurement of zero point: after a required number of measurement cycles are completed, switch the third valve 3 to change the gas flow path to sample chamber 7, first pump 5, third valve 3, filter 16, electrochemical sensor 6 and sample chamber 7, so that the gas passes through the filter 16 before it flows through the sensor, in that state, the response current of the sensor is zero current after the active component is filtered.

Embodiment 4

Figure 4:
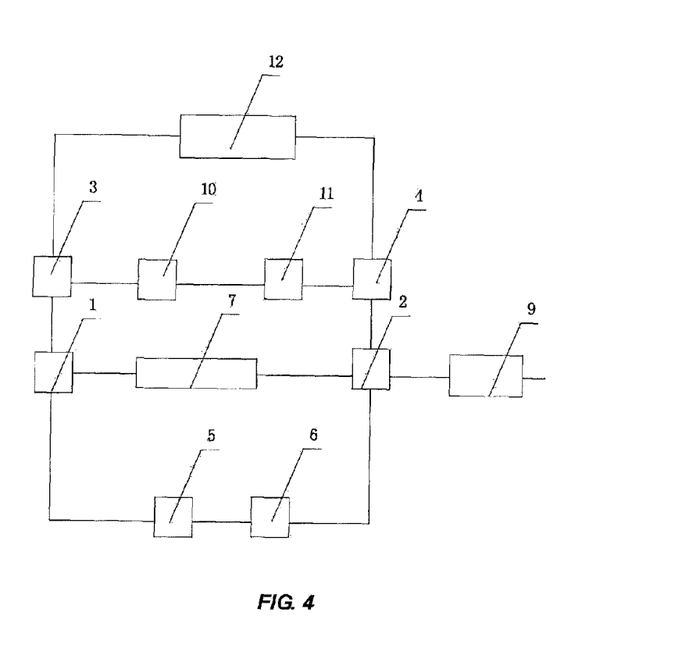
FIG. 4 is a schematic structural diagram of the device in embodiment 4 of the disclosure.

FIG. 4 shows a fourth gas path design that implements the measurement method disclosed in the disclosure. The device consists of a sample chamber 7, a second sample chamber 12, an electrochemical sensor 6, a first pump 5, a first valve 1, a second valve 2, a third valve 3 and a fourth valve 4, wherein, the sample chamber 7, electrochemical sensor 6, first pump 5, first valve 1 and second valve 2 are connected through a pipeline to form a first circulating gas path; the second sample chamber 12, a second filter 11, a third pump 10, the third valve 3 and the fourth valve 4 are connected through a pipeline to form a second circulating gas path, and the two circulating gas paths are connected in parallel with each other; the sample chamber 7 is a slender pipeline, the volume of the sample chamber 7 is greater than 95% (equal to 99.5%) of the total volume of the circulating gas path, a gas flows in the sample chamber 7 in a manner of piston flow in the process of analysis, and the sample chamber 7 is used to store the fluid sample to be analyzed; the electrochemical sensor is enclosed in the circulating flow path, and is used to measure a response value and electrolyze the electrochemical active component to be measured; the pump is used to drive the fluid to circulate in the circulating flow path, so that the fluid can pass through the sensor at least twice, the flow rate of the circulating gas can be obtained from the volume of the gas chamber and the cycle period.

The actual measurement process is carried out through the following three steps:

(1) Sampling: switch the first valve 1, second valve 2, third valve 3 and fourth valve 4, so that the gas is pumped by the second pump 9 through two ways into the sample chamber 7 and the second sample chamber 12, i.e., in one way, the gas is pumped through the first valve 1, sample chamber 7, second valve 2 and second pump 9 into the sample chamber 7; in the other way, the gas is pumped through the first valve 1, third valve 3, second sample chamber 12, fourth valve 4, second valve 2 and second pump 9 into the second sample chamber 12.

(2) Circulation and measurement: switch the first valve 1 and second valve 2, and start the first pump 5 at the same time, so that the gas sample in the sample chamber 7 circulates through the first valve 1, first pump 5, electrochemical sensor 6, second valve 2, and then returns to sample chamber 7 under the action of the circulating pump, to carry out measurement and analysis in two circulation cycles.

(3) Measurement of zero point:

It is carried out in two steps: first, as the cyclic analysis is executed, switch the third valve 3 and fourth valve 4, and start the third pump at the same time, so that the gas in the sample chamber 7 flows through the third valve 3, first pump 5, second filter 11, fourth valve 4, returns to the second sample chamber 12, and circulates in that way under the action of the pump, since the element 11 is a filter for filtering active substances, such as active carbon or potassium permanganate, etc., the active component is removed by absorption or reaction when gas flow passes through the filter; thus, the gas returning to the sample chamber after a circulation cycle is zero gas after the active component is filtered off.

After two measurement cycles are completed, switch the first solenoid valve 1, second valve 2, third valve 3 and fourth valve 4, and start the first pump 5 to change the gas flow direction, so that the gas flows through the second sample chamber 12, third valve 3, first valve 1, first pump 5, electrochemical sensor 6, third valve 3, fourth valve 4, and returns to the second sample chamber 12, and circulates in that way, in this state, the gas flowing in the pipeline is zero gas, and the response value of the sensor is zero response value.

Embodiment 5

Here the method and device for gas detection in the disclosure will be described with reference to FIG. 2. The device consists of a sample chamber 7, an electrochemical sensor 6, a first pump 5, a first valve 1, a second valve 2, a third valve 3 and a fourth valve 4, wherein, the sample chamber 7, electrochemical sensor 6, first pump, first valve 1, second valve 2, third valve 3 and fourth valve 4 and pipeline forms a closed circulating flow path; preferably, the pipeline is composed of capillary tubes, and the internal volume of the capillary tube is smaller than 5% of the total volume of the circulating flow path, optimally smaller than 1% of the total volume of the circulating flow path; the sample chamber is constructed in a way that the gas flow in it is piston flow during cyclic analysis; preferably the sample chamber is a slender pipeline in structure, and the total volume of the sample chamber is greater than 95% of the total volume of the circulating flow path, optimally greater than 99% of the total volume of the circulating flow path; the electrochemical sensor is enclosed in the circulating flow path, and is used to measure a response value and electrolyze the electrochemical active component to be measured; the pump drives the gas to circulate in the circulating flow path, and the flow rate of the circulating gas can be obtained from the volume of the gas chamber and the cycle period.

To carry out analysis, the first step is sampling: the valves are opened, and the gas is pumped by externally connecting the second pump 9 into the sample chamber, or, the sample can be directly fed into the sample chamber, so that the sample chamber is filled with the sample to be tested.

Then, switch the first valve 1, second valve 2, third valve 3 and fourth valve 4, and start the first pump 5 at the same time, the sample is electrolyzed by the sensor in three circulation cycles under the action of the circulating pump. The response value of the sensor whenever the gas passes through the sensor can be expressed with the following measurement equation:

$$i_0 = kC_0 + k_0 \quad (3)$$

$$i_1 = kC_1 + k_0 \quad (4)$$

$$kC_2 + k_0 \quad (5)$$

Wherein, $i_0$, $i_1$ and $i_2$ are response values of the sensor in the measurement cycles, respectively, k is the sensitivity of the sensor, $k_0$ is the background current of the sensor, $C_0$, $C_1$ and $C_2$ are initial concentration of the sample, concentration of the sample measured in the second measurement cycle, and concentration of the sample measured in the third measurement cycle, respectively, there are five unknown quantities: k, $K_0$, $C_0$, $C_1$, and $C_2$.

According to Faraday's law, the mass equation of the relationship between the quantity of sample consumed by electrolysis and the resultant change of concentration of the sample in each measurement cycle carried out by the sensor can be expressed as:

$$nFV(C_1 - C_0) = i_0 * t \quad (6)$$

$$nFV(C_2 - C_1) = i_0 * t \quad (7)$$

Wherein, n is the number of electronics involved in the reaction, F is Faraday constant, V is the volume of the sample chamber, and t is the cycle period.

From the above five equations, the parameters, including sample concentration, sensor sensitivity, and background current, can be solved, without calibrating the sensor with a standard gas.

It is seen from this embodiment: the method can be used to directly ascertain the concentration of the measured material, without calibrating the sensor before the measurement; in addition, the calibration parameters (e.g., sensitivity and background current) of the sensor can be directly solved with the method. Since the sensor calibration parameters are calculated in an actual measurement process, the method can be regarded as a self-calibration method. In addition, since the method utilizes the difference between two response values of the sensor, the contributions of temperature, pressure, flow, and interfering materials, which are identical in each measurement, is deducted. Therefore, compared with the conventional method, which utilizes signals that contain these contributing factors, the method has higher sensitivity, selectivity, and stability.

Though some examples of measurement with an electrochemical sensor are described in above embodiments, the actual application is not limited to those examples. If other types of sensors are used, such as sensors that measure concentration by measuring the change of material mass or heat, the analytical method and device described above are also applicable, provided that the change of quantity in the process of measurement meets the mass equation and can be calculated.

An inducted mathematical representation of the method is given below:

1. A sample with concentration $C_0$ to be measured is measured by the same chemical sensor for n times successively. In the $j^{th}$ measurement, the inlet concentration and outlet concentration of the sensor are $C_{j-1}$ and $C_j$, respectively, and the response value $S_{j-1}$ follows the measurement equation (1), i.e.:

$$S_{j-1} = F(C_{j-1}, k_1, k_2 \ldots k_m) \, j=1,2,\ldots,n \quad (8)$$

or $$S_{j-1} - S_j = F(C_{j-1}, k_1, k_2 \ldots k_m) - F(C_j, k_1, k_2 \ldots k_m) \quad (9)$$

FIG. 1 shows an example of successive cyclic measurement.

2. The concentration change of the tested material passing through the chemical sensor follows the following mass equation (see FIG. 1):

$$C_{j-1} - C_j = R(C_{j-1}, C_j, K_1, K_2 \ldots K_p)/V \quad (10)$$

In above equation, R is the average consumption rate of the tested material in the chemical sensor, wherein, $K_j$ is a rate constant; $K_j$ and V are stay time of the sample in the chemical sensor and the volume of gas, respectively, and they are known design data.

The concentration $C_0$ of the measured material and the calibration parameters can be ascertained by solving the simultaneous equations (9) and (10), wherein, the number of successive measurement n is determined by the condition for a unique solution that meets the system of equations (the number of independent equations is equal the number of unknown quantities, i.e., 2n=(n+1)+m+p), i.e., it is the required number of measurement.

$$n = m + p + 1 \quad (11)$$

Thus, by measuring the same sample for several times and solving the system of equations shown above, according to the correlation among the measurement, the concentration of the tested sample and the calibration parameter of the sensor used in the measurement can be calculated.

Embodiment 6

Figure 5:
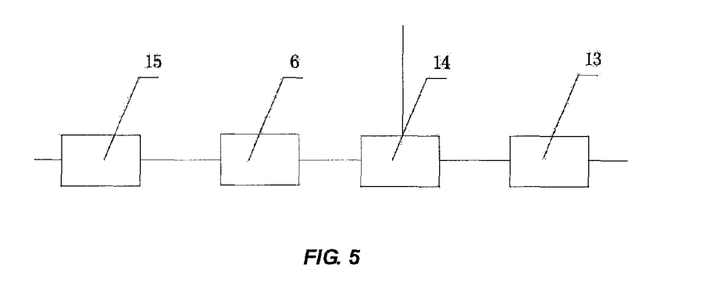
FIG. 5 is a schematic structural diagram of the device in embodiment 6 of the disclosure.
Figure 6:
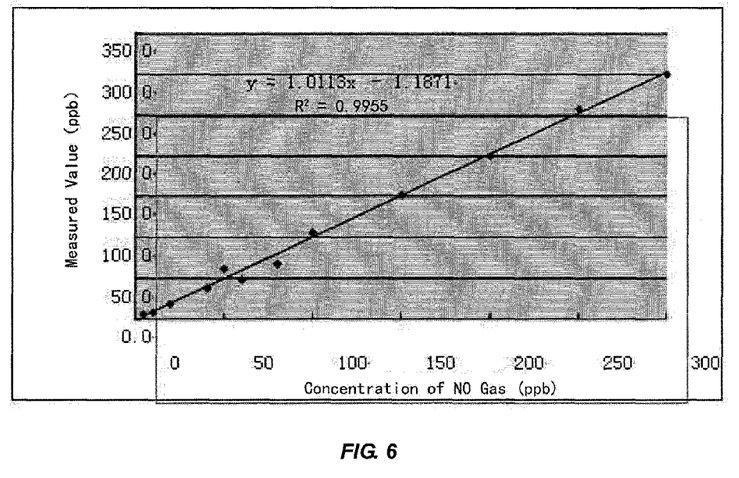
FIG. 6 is a diagram of comparison between measured value obtained with the method disclosed in the disclosure and the actual concentration of gas.

Hereunder another method and a device in the disclosure will be described with reference to FIG. 5. The device consists of a piston sample chamber 13, a three-way valve 14, an electrochemical sensor 6, and a buffer chamber 15, wherein, the piston sample chamber 13, three-way valve 14, electrochemical sensor 6, and buffer chamber 15 are connected in series through a pipeline, and one way of the three-way valve 14 is used to receive a sample to be analyzed; the piston sample chamber 13 is used to store the fluid to be analyzed and drive the fluid to flow to and fro in the pipeline and the sensor at a constant flow rate; the electrochemical sensor is used to measure a response value and electrolyze the electrochemical active component to be measured; the buffer chamber 15 is used to store the fluid temporarily.

Sampling: switch the three-way valve 14 and pull the piston to collect a sample to be analyzed.

First analysis: switch the three-way valve 14, and push the piston of the sample chamber at a fixed rate, so that the gas passes through the electrochemical sensor 6 and buffer chamber 15, and the original gas in the buffer chamber 15 is discharged, to log the response value of the sensor.

Second analysis: pull the piston of the sample chamber at the same rate, so that the sample gas passes through the buffer chamber 15 and electrochemical sensor 6 and returns to the sample chamber, to accomplish a second measurement cycle.

The above measurement can be carried out to and fro, to obtain a required measurement and system of mass equations, so as to solve the sample concentration and sensor parameters.

In this embodiment, the buffer chamber 15 can be replaced with a gas sample bag or a sample chamber with a movable piston.

The piston sample chamber 13 can be implemented by a combination of pump, valve, and gas bag. The gas pumping direction can be switched by means of the valve, so that the gas to be analyzed flows to and fro between the sample chamber and the buffer chamber.

Since there is no essential difference between liquid samples and gas samples in the analytical method, the method described in above embodiments is also applicable to analysis of liquid samples.

The following application example explains how to use the method disclosed in the disclosure to measure nitrogen oxide in the environment or exhaled from human body.

This example explains how to use the disclosure to measure nitrogen oxide in the environment or exhaled from human body. As a marker of airway inflammation, exhaled nitrogen oxide can be used to diagnose, keep track of, and monitor respiratory diseases, such as asthma. In European and American countries, standards are established to encourage and recommend such non-intrusive diagnostic techniques, and these standards specify that the detection accuracy and lower limit should not be inferior to 5 ppb. For detection at such a low concentration, the sensitivity of a gas sensor may have a quick and obvious drift, owing to the effect of the ambient humidity and other interfering gasses. More frequent and professional calibration is required, when compared with detection at higher concentrations.

For example, in patent US20040082872, high-sensitivity detection and analysis of exhaled gas is realized by strictly controlling the temperature (22° C.) and humidity (70%) of the sample gas and the temperature (22° C.) of the gas sensor, and the drift of sensitivity incurred by temperature and humidity is decreased to some degree. However, a sensor will still have quick and obvious sensitivity drift after it is used for many times, owing to the effect of other interfering gasses and ageing or inactivation of the detecting electrodes, in that case, the sensor has to be replaced, or external calibration has to be carried out by specialists with the method specified by the manufacturer periodically (e.g., once in every 7 days or once after a specified number).

In contrast, since the analytical method disclosed in the disclosure deducts the effect of zero and sensitivity drift of the sensor, it is unnecessary to calibrate the sensor, and it is unnecessary to control the measuring conditions like the case described in patent US20040082872 at constant temperature and humidity values when the sensor is used for detecting exhaled nitrogen oxide, thus, the measuring device is simplified, and the accuracy and reliability of measurement are improved.

The testing device in this embodiment is shown in FIG. 3.

In the measurement process, NO gas samples are prepared at 10 concentration levels (5, 10, 20, 40, 60, 80, 150, 200, 250 and 300 ppb) with a range of 5~300 ppb from a standard gas, after the gas sample is fed into a sample chamber 7 and replace the original gas in the sample chamber 7 completely, the first valve 1 and second valve 2 are shut off, and the first pump 5 is started at the same time, to carry out cyclic electrolysis. After the sample gas circulates in the pipeline and is measured for three cycles, the concentration of the sample gas is calculated with an obtained curve. FIG. 5 shows the result obtained after three measurements are completed and the mean value of the measurements is plotted against the concentration of the prepared gas, and a regression analysis is carried out. It can be seen from the result: the result obtained with the method essentially matches the concentration of prepared gas, and the linear dependence is 0.996 within the range of 5~300 ppb.

While the object, technical scheme, and beneficial effects of the disclosure are detailed above in some embodiments, it should be understood that those embodiments are exemplary instead of constituting any limitation to the disclosure, any modification, equivalent replacement, or improvement made without departing from the spirit and principle of the disclosure shall be deemed as falling in the scope of protection of the disclosure.

The invention claimed is:

1. A method for measuring material concentration in a fluid, the method comprising:
   driving a sample to be tested to pass through a chemical sensor at least twice,
   logging a response value of the chemical sensor in each pass-through;
   establishing a simultaneous system of equations from a measurement equation relationship between the response value obtained by the chemical sensor in each pass-through and the material concentration and a mass equation relationship between a change of material concentration resulting from physical and chemical reactions in each pass-through and a change of mass, a change in electric quantity, and a change in heat in the physical and chemical reactions, and
   solving the simultaneous system of equations to ascertain the material concentration of the sample and one or more calibration parameters of the chemical sensor.

2. The method according to claim 1, further comprising:
   if a concentration of an electrochemical active material in the fluid is to be measured, the chemical sensor is an electrochemical current sensor configured such that the tested sample passes through the electrochemical sensor at least twice, and the response value in each pass-through is logged; and
   establishing a simultaneous system of equations from the measurement equation relationship between the response value of the electrochemical sensor in each pass-through and the material concentration and the mass equation relationship between the change of material concentration incurred by electrolysis in each pass-through and the change in electric quantity, and then the simultaneous system of equations is solved, to ascertain the material concentration of the sample and one or more calibration parameters of the chemical sensor.

3. A method for measuring material concentration in a fluid, comprising:
   driving a sample to be tested to pass through an electrochemical sensor at least twice,
   logging a response value of the electrochemical sensor in each pass-through, wherein, one response value is used to measure a zero point of the electrochemical sensor;
   establishing a simultaneous system of equations from a measurement equation relationship between a current value of the electrochemical sensor obtained in each pass-through and a concentration of the sample and a mass equation relationship between a concentration change of the sample resulting from electrolysis in each pass-through and a change in electric quantity; and
   solving the simultaneous system of equations to ascertain the material concentration of the sample and one or more calibration parameters of the electrochemical sensor.

* * * * *

UNITED STATES PATENT AND TRADEMARK OFFICE
CERTIFICATE OF CORRECTION

PATENT NO. : 9,970,894 B2
APPLICATION NO. : 14/408526
DATED : May 15, 2018
INVENTOR(S) : Ray Xie et al.

It is certified that error appears in the above-identified patent and that said Letters Patent is hereby corrected as shown below:

On the Title Page
In ITEM (72) Inventors: change "Ray Xie, Jiangsu (CN); Jie Han, Jiangsu (CN); Lijun Shen, Jiangsu (CN); Yiping Han, Jiangsu (CN)" to --Ray Xie, Wuxi, Jiangsu (CN); Jie Han, Wuxi, Jiangsu (CN); Lijun Shen, Wuxi, Jiangsu (CN); Yiping Han, Wuxi, Jiangsu (CN)--

In ITEM (73) Assignee: change "Woxi, Jiangsu (CN)" to --Wuxi, Jiangsu (CN)--

In the Specification
    Column 11,    Line 5,    change "$kC_2+k_o$" to --$i_2=kC_2+k_o$--

In the Claims
Claim 2,    Column 14,    Line 43,    change "one or more" to --the one or more--

Signed and Sealed this
Tenth Day of July, 2018

Andrei Iancu
*Director of the United States Patent and Trademark Office*